United States Patent [19]

Totani et al.

[11] 4,359,425
[45] Nov. 16, 1982

[54] ORGANO-PLATINUM COMPLEX

[75] Inventors: Tetsushi Totani, Takarazuka; Kenji Yamaguchi, Osaka, both of Japan

[73] Assignee: Shionogi & Co., Ltd., Osaka, Japan

[21] Appl. No.: 249,455

[22] Filed: Mar. 31, 1981

[30] Foreign Application Priority Data

Apr. 30, 1980 [JP] Japan .................... 55/58359

[51] Int. Cl.³ .............................................. C07F 15/00
[52] U.S. Cl. .................................. 260/429 R; 424/287
[58] Field of Search ......................... 260/429 R, 345.7

[56] References Cited

U.S. PATENT DOCUMENTS

| | | | |
|---|---|---|---|
| 2,892,790 | 7/1975 | Tobe et al. | 260/429 R |
| 4,115,418 | 9/1978 | Gale et al. | 260/429 R |
| 4,137,248 | 1/1979 | Gale et al. | 260/429 R |
| 4,140,707 | 2/1979 | Cleare et al. | 260/429 R |
| 4,169,846 | 10/1979 | Kidani et al. | 260/429 R |
| 4,200,583 | 4/1980 | Kidani | 260/429 R X |
| 4,234,500 | 11/1980 | Hoeschele | 260/429 R |
| 4,250,189 | 2/1981 | Hydes et al. | 260/429 R |
| 4,255,347 | 3/1981 | Kidani et al. | 260/429 R |
| 4,256,652 | 3/1981 | Kidani et al. | 260/429 R |

OTHER PUBLICATIONS

Braddock et al., Chemico-Biological Interactions (Amsterdam) vol. 11 (3) 151, 153, 155 (1975).

Primary Examiner—Helen M. S. Sneed
Attorney, Agent, or Firm—Wenderoth, Lind & Ponack

[57] ABSTRACT

Organo-platinum complexes of the following formula having excellent antitumor actions:

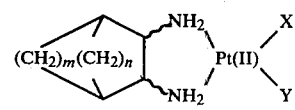

X and Y each or taken together is a mono- or bi-functional ligand selected from the group consisting of halogeno, nitrato, sulfonato, monocarboxylato (mono-functional), sulfato, and dicarboxylato (bi-functional);

and each of n and m is an integer of 1 or 2.

19 Claims, No Drawings

ORGANO-PLATINUM COMPLEX

This invention relates to antitumor agents. More particularly, this invention relates to organo-platinum complexes having potent antitumor actions.

BACKGROUND OF THE INVENTION

It has been known that some kinds of platinum complexes have antitumor actions; particularly, cisplatin [cisdiamminedichloroplatinum(II)] has been used clinically in treatment of malignancy, for example, disseminated testicular and ovarian carcinoma. Cisplatin, however, has serious side effects such as renal toxicity, myelosuppression, and ototoxicity. Recently, the occurence of malignancy and death rate owing thereto are on the increase, and it is desirable to develop antitumor agents of which the activity is strong but less toxic. In order to achieve the above purpose, chemical modification of platinum complexes has been attempted extensively. Representatives of the platinum complexes disclosed in literatures are malonato (1,2-diaminocyclohexane)platinum(II)[Japanese Unexamined Patent Publication No. 53-31648], sulfato (1,2-diaminocyclohexane)platinum(II)[Japanese Unexamined Patent Publication No. 54-44620], and the like.

DETAILED DESCRIPTION OF THE INVENTION

The compounds of this invention are represented by the following formula:

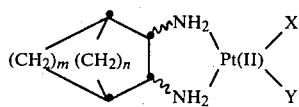

[I]

(wherein X and Y each or taken together is a mono- or bi-functional ligand selected from the group consisting of halogeno, nitrato, sulfonato, monocarboxylato, (mono-functional), sulfato, and dicarboxylato (bi-functional);

and each of n and m is an integer of 1 or 2)

In the above definition, the halogeno means chloro, bromo, iodo, and the like, preferably chloro. Sulfonato includes $C_1$ to $C_5$ alkanesulfonato and $C_6$ to $C_8$ arylsulfonato. Representatives of the $C_1$ to $C_5$ alkanesulfonatoes are methanesulfonato, ethanesulfonato, propanesulfonato, isopropanesulfonato, butanesulfonato, isobutanesulfonato, sec-butanesulfonato, t-butanesulfonato, pentanesulfonato, and the like. Representative of the $C_6$ to $C_8$ arylsulfonatoes are benzenesulfonato, toluenesulfonato, xylenesulfonato, and the like. Monocarboxylato means saturated or unsaturated $C_1$ to $C_7$ monocarboxylato, including formato, acetato, propionato, butyrato, isobutyrato, valerato, acrylato, propionato, methacrylato, crotonato, isocrotonato, and the like. Preferable monocarboxylato is $C_2$ to $C_6$ monocarboxylato, preferably acetato. Dicarboxylato means saturated or unsaturated $C_2$ to $C_{10}$ dicarboxylato, including oxalato, malonato, succinato, maleato, fumarato, phthalato, hemimellitato, and the like, preferably, oxalato, malonato, or hemimellitato. The above monocarboxylato and dicarboxylato may optionally be substituted by halogen or hydroxy as exemplified by chloroacetato, gluconato, glucuronato, and the like, and these are also included within the scope of this invention.

In the above formula [I], when n differs from m, the configuration of the aminoes on the bicyclic structure is exocis or trans.

Representatives of the compounds [I] are as follows:

(1) dichloro[exo,cis-2,3-diaminobicyclo(2.2.1)heptane]platinum(II);

(2) dinitrato[exo,cis-2,3-diaminobicyclo(2.2.1)heptane]platinum(II);

(3) sulfato[exo,cis-2,3-diaminobicyclo(2.2.1)heptane]platinum(II);

(4) malonato[exo,cis-2,3-diaminobicyclo(2.2.1)heptane]platinum(II);

(5) bis(chloroacetato)[exo,cis-2,3-diaminobicyclo(2.2.1)heptane]platinum(II);

(6) hemimellitato[exo,cis-2,3-diaminobicyclo(2.2.1)heptane]platinum(II);

(7) oxalato[exo,cis-2,3-diaminobicyclo(2.2.1)heptane]platinum(II);

(8) bis(glycolato)[exo,cis-2,3-diaminobicyclo(2.2.1)heptane]platinum(II);

(9) bis(glucuronato)[exo,cis-2,3-diaminobicyclo(2.2.1)heptane]platinum(II);

(10) dichloro[exo,cis-2,3-diaminobicyclo(2.2.2)octane]platinum(II); and

(11) bis(gluconato)[exo,cis-2,3-diaminobicyclo(2.2.2)octane]platinum(II).

PREPARATION

The compounds [I] of this invention are readily prepared from the compounds of the formula [II] in the well-known conventional manner.

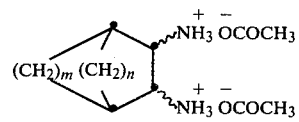

[II]

(wherein n and m are the same as mentioned above)

(1) In the case of X and Y each being halogen:

The compounds [II] are reacted with alkali metal salts of tetrahalogenoplatinate(II) to give the compounds [Ia] (X and Y each is halogen in [I]). It is preferred to employ the potassium salts as the alkali metal salts of tetrahalogenoplatinate(II). This reaction proceeds in weak alkaline conditions and is preferably carried out in the presence of sodium hydrogen-carbonate. It ordinarily takes 5 to 10 hours to complete this reaction.

(2) In the case of X and/or Y being nitrato:

The compounds [Ia] are reacted with silver nitrate in an aqueous medium to give the compounds [I] wherein X and/or Y are nitrato. When one molar equivalent of silver nitrate is employed to the compounds [Ia], the compounds [Ib] (in [I] either X or Y is nitrato) are given, and when two molar equivalents of silver nitrate is employed, the compounds [Ic] (in [I] both of X and Y are nitrato) are given. This reaction is carried out under protection from light and completed within a period of 2 to 5 days.

(3) In the case of X and/or Y being sulfonato:

The compounds [Ia] are reacted with silver sulfonate, for example, silver methanesulfonate and silver benzenesulfonate to give the compounds [I] wherein X and/or Y are sulfonato. When one molar equivalent of silver sulfonate is employed to the compounds [Ia], the compounds [Id] (in [I] either X or Y is sulfonato) are given, and when two molar equivalents of silver sulfonate is employed, the compounds [Ie] (in [I] both of X and Y are sulfonato) are given.

(4) In the case of X and Y taken together being sulfato:

The compounds [Ia] are reacted with silver sulfate to give the compounds [If] (in [I] X and Y taken together is sulfato). It is preferred to effect this reaction at room temperature under protection from light, and the reaction is completed within a period of 1 to 3 days.

(5) In the case of either X or Y being nitrato and the other being monocarboxylato:

The compounds [Ic] are reacted with alkali metal salts of monocarboxylic acid to give the compounds [Ig] (in [I] either X or Y is nitrato and the other is monocarboxylato). It is preferred to one molar equivalent of alkali metal salts of monocarboxylic acid to the compounds [Ic].

(6) In the case of X and Y each or taken together being monocarboxylato or dicarboxylato:

The compounds [Ic] are reacted with monocarboxylic acids, dicarboxylic acids, or the alkali metal salts thereof in water to give the compounds [Ih] (in [I] X and Y each is monocarboxylato, or X and Y taken together represent dicarboxylato). This reaction is carried out under cooling or heating and ordinarily completed within a period of several ten minutes to several days, which time depends on the species of carboxylic acids used, and variation and number of the substituents.

The above starting compounds [II] are readily prepared from the compounds of the formula [III] shown below according to the manner described in Journal of the American Chemical Society, 89, 3005 (1967).

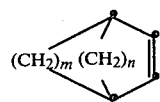
[III]

(wherein n and m are the same as mentioned above)

The compounds [III] are well-known compounds, among which the compounds [III] (m=n=1) have been disclosed in Tetrahedron Letters 1968, 2789, the compounds [III] (m=2 and n=1, or m=1 and n=2) are commercially available as 2-norbornene, and the compounds [III] (m=n=2) have been disclosed in Journal of the American Chemical Society, 76, 5396 (1954).

EFFECT

The compounds [I] of this invention have potent antitumor actions. For example, the activities of representative compounds [I] of this invention are shown below.

(Test Method)

Leukemia L 1210 ascites cells ($10^5$ cells) in mouse were intraperitoneally inoculated to $BDF_1$ mice. On the next day, the predetermined amount of the test compounds shown below was administered. Eight to ten mice were employed in a control group, and four to seven mice were employed in a test group.

(Evaluation of the effect)

From the average survival days in the test group and those of the control group, the increase of lifespan (ILS) was calculated according to the following expression.

$$ILS (\%) = \frac{\text{Average survival days in test group} - \text{Average survival days in control group}}{\text{Average survival days in control group}} \times 100$$

(Test compounds)

(1) dichloro[exo,cis-2,3-diaminobicyclo(2.2.1)heptane]platinum(II)

(2) dinitrato[exo,cis-2,3-diaminobicyclo(2.2.1)heptane]platinum(II)

(3) sulfato[exo,cis-2,3-diaminobicyclo(2.2.1)heptane]platinum(II)

(4) oxalato[exo,cis-2,3-diaminobicyclo(2.2.1)heptane]platinum(II)

(5) malonato[exo,cis-2,3-diaminobicyclo(2.2.1)heptane]platinum(II)

(6) bis(glucuronato)[exo,cis-2,3-diaminobicyclo(2.2.1)heptane]platinum(II)

(Comparative compounds)

(7) dichloro(cis-diamine)platinum(II)

(8) dichloro(1,2-diaminocyclohexane)platinum(II)

| Test Compound | Dosage (mg/kg) | Numbers of mice employed | ILS (%) | Numbers of survivors over 30 days |
|---|---|---|---|---|
| (1) | 0 × 1 | 8 | | |
| | 1 × 1 | 7 | 25 | |
| | 2 × 1 | 7 | 51 | |
| | 5 × 1 | 7 | >126 | 2 |
| | 10 × 1 | 7 | >143 | 3 |
| | 20 × 1 | 7 | −21 | |
| (2) | 0 × 1 | 8 | | |
| | 1 × 1 | 7 | 32 | |
| | 2 × 1 | 7 | 51 | |
| | 5 × 1 | 7 | 80 | |
| | 10 × 1 | 7 | >151 | 4 |
| | 20 × 1 | 7 | −18 | |
| (3) | 0 × 1 | 8 | | |
| | 1 × 1 | 7 | 21 | |
| | 2 × 1 | 7 | 31 | |
| | 5 × 1 | 7 | 48 | |
| | 10 × 1 | 7 | >221 | 5 |
| | 20 × 1 | 7 | −35 | |
| (4) | 0 × 1 | 10 | | |
| | 1 × 1 | 7 | 3 | |
| | 2 × 1 | 7 | 13 | |
| | 5 × 1 | 7 | >54 | 1 |
| | 10 × 1 | 7 | >79 | 1 |
| | 20 × 1 | 7 | >149 | 4 |
| (5) | 0 × 1 | 7 | | |
| | 5 × 1 | 7 | 16 | |
| | 10 × 1 | 7 | 20 | |
| | 20 × 1 | 7 | 31 | |
| | 50 × 1 | 5 | >84 | 1 |
| | 100 × 1 | 7 | −18 | |
| (6) | 0 × 1 | 10 | | |
| | 1 × 1 | 7 | 4 | |
| | 2 × 1 | 7 | 17 | |
| | 5 × 1 | 7 | 27 | |
| | 10 × 1 | 7 | >67 | 1 |
| | 20 × 1 | 7 | >126 | 2 |
| | 50 × 1 | 7 | >43 | 1 |
| (7) | 0 × 1 | 10 | | |
| | 1 × 1 | 7 | 9 | |
| | 2 × 1 | 7 | 11 | |
| | 5 × 1 | 7 | 29 | |
| | 10 × 1 | 7 | >84 | 1 |
| | 20 × 1 | 4 | −26 | |
| (8) | 0 × 1 | 10 | | |
| | 1 × 1 | 7 | 15 | |
| | 2 × 1 | 7 | 20 | |
| | 5 × 1 | 7 | >67 | 1 |

| Test Compound | Dosage (mg/kg) | Numbers of mice employed | ILS (%) | Numbers of survivors over 30 days |
|---|---|---|---|---|
| | 10 × 1 | 7 | >129 | 2 |
| | 20 × 1 | 7 | −7 | |

As seen from the above table, the compounds [I] of this invention have potent antitumor actions.

HOW TO USE

The compounds [I] of this invention can be administered parenterally to humans or animals in treatment of various kinds of malignancy. In using, the compounds [I] may be dissolved or suspended in a suitable solvent for injection (e.g. distilled water for injection, isotonic sodium chloride solution, ethanol, glycerin, propylene glycol, oleave oil, peanut oil), and administered intravenously, intramuscularly, or subcutaneously. In preparations for injection, the compounds [I] may be contained in ampoules in a form of solution or suspension; alternatively, it is appropriate to keep the compounds [I] in ampoules or vials in a form of crystals, powder, microcrystals, lyophilizate, and the like and to dissolve or suspend immediately before using. If necessary, stabilizing agents may be added.

When used in treatment of tumors, the compounds [I] may be administered parenterally to an adult at a single or divided doses of 1 to 100 mg 1 to 3 times a day. But it is appropriate to optionally increase or decrease the dosage according to the age, condition, or anamnesis of patients.

The following examples are provided to further illustrate this invention.

EXAMPLE 1

Dichloro[exo,cis-2,3-diaminobicyclo(2.2.1)heptane]-platinum(II)

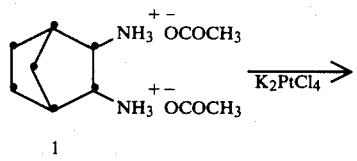

1

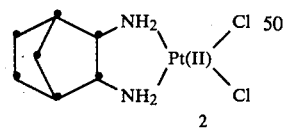

2

To a solution of diacetato exo,cis-2,3-diaminobicyclo(2.2.1)heptane 1 (300 mg; 1.22 mmoles) in water (3 ml) are added a solution of potassium tetrachloroplatinate(II) (468 mg; 1.23 mmoles) in water (6 ml) and then solid sodium hydrogencarbonate (206 mg; 2.45 mmoles), and the mixture is shaken, by which carbon dioxide is vigorously generated. After subsidence of carbon dioxide evolution, the reaction mixture is stirred at room temperature for 8 hours. The resulting solid is collected by filtration, washed with water, acetone, and then ether, and dried under reduced pressure to give the title compound 2 (303 mg) as pale yellowish green crystals (first crop). The mother liquor is allowed to stand overnight to give an additional crop of the title compound 2 (49 mg) as yellow crystals (second crop).

Total yield 352 mg (74%)

mp. >300° C.

Elemental Analysis:

Calcd (for $C_7H_{14}N_2PtCl_2$)(%): C, 21.44; H, 3.60; N, 7.14; Cl, 18.08.

Found (%): C, 21.40; H, 3.50; N, 6.94; Cl, 18.16. IR: $v_{max}^{Nujol}$ 3205, 3110 ($-NH_2$) cm$^{-1}$.

EXAMPLE 2

Dinitrato[exo,cis-2,3-diaminobicyclo(2.2.1)heptane]-platinum(II)

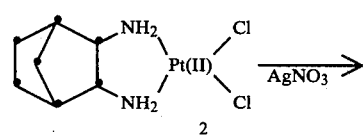

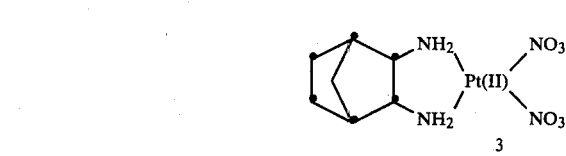

3

To a suspension of Compound 2 (392 mg; 1 mmole) in water (35 ml) is added silver nitrate (340 mg; 2 mmoles), and the reaction vessel is wrapped in a sheet of aluminum foil in order that the reaction mixture is shielded from light. The mixture is stirred for 3 days, and the resulting colorless precipitate (silver chloride) is removed by filtration. The excess amount of silver nitrate remaining in the filtrate is decomposed with 0.5% aqueous solution of potassium chloride, which is added to the filtrate until no turbidity produced. The filtrate is evaporated to dryness with a rotary evaporator, and the resulting residue is dried at nearly 55° C. under reduced pressure to give the title compound 3 (384 mg) in 86% yield.

mp. about 200° C. (decomposition)

Elemental Analysis:

Calcd (for $C_7H_{14}N_4O_6Pt$)(%) C, 18.88; H, 3.17; N, 12.58.

Found (%) C, 18.32; H, 3.24; N, 12.32. IR: $v_{max}^{Nujol}$ 3240, 3150 ($-NH_2$), 1466, 1274 ($-NO_3$) cm$^{-1}$.

EXAMPLE 3

Sulfato[exo,cis-2,3-diaminobicyclo(2.2.1)heptane]-platinum(II)

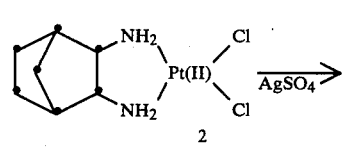

2

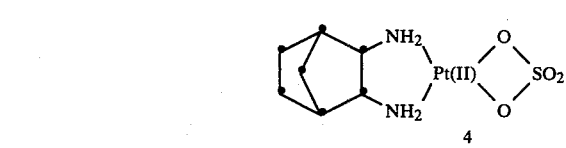

4

To a suspension of Compound 2 (275 mg; 0.7 mmole) in water (30 ml) is added silver sulfate (218 mg; 0.7 mmole), and the mixture is stirred at room temperature for 2 days under protection from light, and then worked up in the same manner as in Example 2 to give the title compound 4 (260 mg) as an yellow material in 80% yield.

mp. about 230° C. (decomposition)

Elemental Analysis:

Calcd (for $C_7H_{14}N_2O_4SPt$)(%): C, 20.15; H, 3.38; N, 6.71; S, 7.68.

Found (%): C, 18.14; H, 3.67; N, 6.30; S, 7.61. IR: $\nu_{max}^{Nujol}$ ~3180, ~3080 (—NH$_2$), 1110, 1023, 940 (—SO$_4$) cm$^{-1}$.

EXAMPLE 4

Malonato[exo,cis-2,3-diaminobicyclo(2.2.1)heptane]-platinum(II)

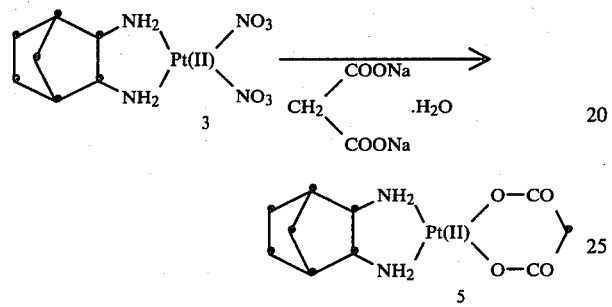

Compound 3 (400 mg; 0.9 mmole) is dissolved in water (20 ml) under heating at 95° C. A solution of sodium malonate monohydrate (150 mg; 0.9 mmole) in water (3 ml) is added thereto, and the mixture is allowed to stand at room temperature for 10 to 20 minutes to yield colorless crystals as precipitates. The reaction mixture is cooled with ice for nearly complete crystallization. The resulting colorless crystals are collected by filtration to give the title compound 5 (287 mg) (first crop). The mother liquor is further concentrated to about 3 ml and allowed to stand overnight to give an additional crop of the title compound 5 (38 mg) (second crop).

Total yield: 325 mg (85%)

mp. about 240° C. (decomposition)

Elemental Analysis:

Calcd (for $C_{10}H_{16}N_2O_4Pt$)(%): C, 28.37; H, 3.81; N, 6.62.

Found (%): C, 27.78; H, 3.71; N, 6.66. IR: $\nu_{max}^{Nujol}$ 3175, 3115 (—NH$_2$), 1662, 1623 (—C=O) cm$^{-1}$.

EXAMPLE 5

Bis(chloroacetato)[exo,cis-2,3-diaminobicyclo(2.2.1)heptane]platinum(II)

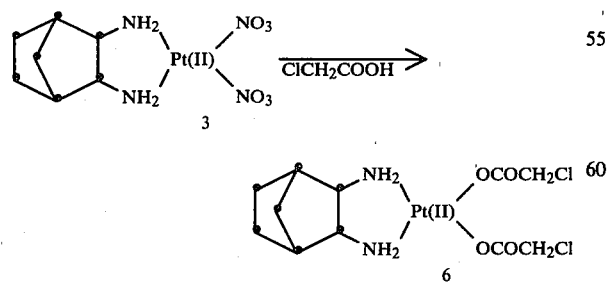

Compound 3 (60 mg; 0.135 mmole) is dissolved in water (3 ml) under heating, and the resultant solution is cooled to room temperature, mixed with chloroacetic acid (86 mg; 0.9 mmole), and allowed to stand in a refrigerator for 3 days. The separated crystals are collected by decantation, washed with a small amount of cold water, and dried under reduced pressure to give the title compound 6 (24 mg) containing water of crystallization (35% yield). This is repeatedly recrystallized from methylene chloride-hexane in order that the water of crystallization may be removed.

mp. 153°–156° C. (decomposition)

Elemental Analysis:

Calcd (for $C_{11}H_{18}N_2O_4Cl_2Pt$)(%): C, 25.99; H, 3.57; N, 5.51.

Found (%): C, 25.48; H, 3.54; N, 5.57. IR: $\nu_{max}^{Nujol}$ 3195, 3100 (—NH$_2$), 1621 cm$^{-1}$.

EXAMPLE 6

Hemimellitato[exo,cis-2,3-diaminobicyclo(2.2.1)heptane]platinum(II)

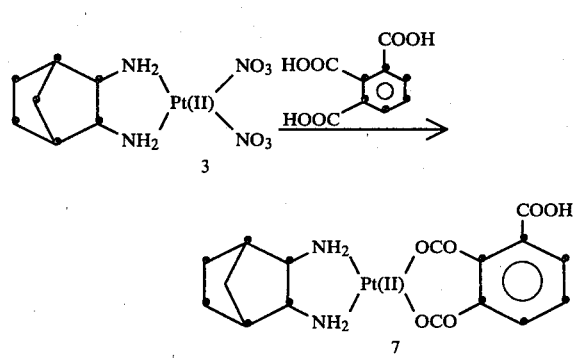

Compound 3 (48 mg; 0.108 mmole) and hemimellitic acid (22.7 mg; 0.108 mmole) are dissolved in water (1.2 ml) under heating, and the resultant solution is allowed to stand at room temperature. After 10 to 15 minutes, the colorless solid is precipitated. After 5 hours, the precipitate is collected by decantation and washed twice with a small amount of water to give the title compound 7 (10 mg) in 17% yield.

mp. about 200° C. (decomposition)

Elemental Analysis

Calcd (for $C_{16}H_{18}N_2O_6Pt$)(%): C, 36.30; H, 3.43; N, 5.29.

Found (%): C, 32.84; H, 3.60; N, 5.54. IR: $\nu_{max}^{Nujol}$ ~3400 (—OH), ~3200, ~3090 (—NH$_2$), 1710, 1603, 1576 (—C=O) cm$^{-1}$.

EXAMPLE 7

Oxalato[exo,cis-2,3-diaminobicyclo(2.2.1)heptane]-platinum(II)

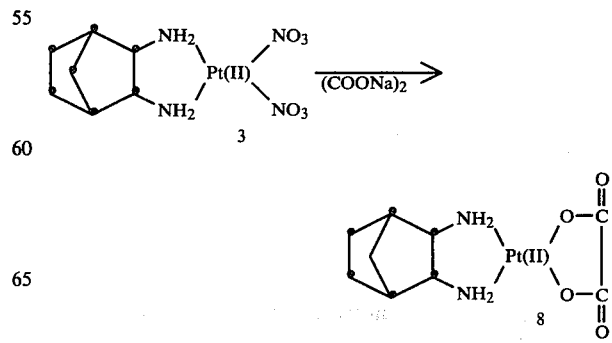

To a solution of Compound 3 (178 mg; 0.4 mmole) dissolved in water (5 ml) under heating is added a solution of sodium oxalate (54 mg; 0.4 mmole) in water (5 ml). The mixture is allowed to stand at room temperature and the precipitated crystals are collected by filtration to give the title compound 8 (122 mg) in 75% yield.

mp. 290°–295° C. (decomposition)

Elemental Analysis:

Calcd (for C$_9$H$_{14}$N$_2$O$_4$Pt)(%): C, 26.41; H, 3.45; N, 6.84.

Found (%): C, 26.35; H, 3.55; N, 6.75. IR: $\nu_{max}^{Nujol}$ 3210, 3110 (—NH$_2$), 1695, 1664 (—C=O) cm$^{-1}$.

EXAMPLE 8

Bis(glycolato)[exo,cis-2,3-diaminobicyclo(2.2.1)heptane]platinum(II)

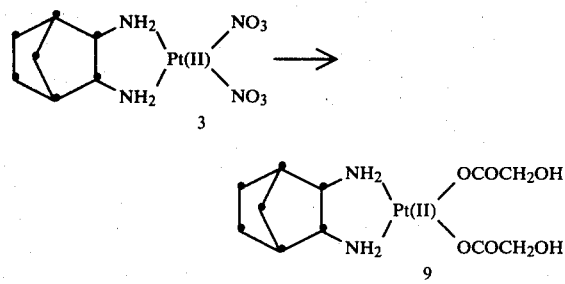

Compound 3 (91 mg; 0.2 mmole) and sodium glycolate (39 mg; 0.4 mmole) are dissolved in water (6 ml) under heating, and the resultant solution is heated at 70° C. for 6 hours. Most of the solvent is evaporated under reduced pressure and the residue is mixed with a large amount of alcohol. The resultant colorless precipitate is collected by filtration and dried under reduced pressure to give the title compound 9 (31 mg) in 33% yield.

mp. 210°–215° C. (decomposition)

IR: $\nu_{max}^{Nujol}$ 3210, 3130 (—NH$_2$), 1618 (—C=O) cm$^{-1}$.

EXAMPLE 9

Bis(glucuronato)[exo,cis-2,3-diaminobicyclo(2.2.1)heptane]platinum(II)

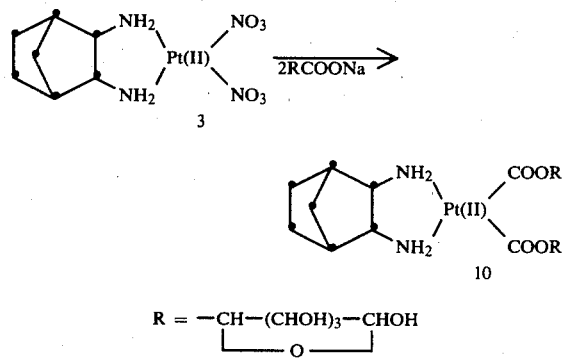

R = —CH—(CHOH)$_3$—CHOH
     |_____O_____|

To a solution of Compound 3 (437 mg; 0.982 mmole) dissolved in water (40 ml) under heating is added sodium D-glucuronate monohydrate (468 mg; 2.00 mmoles), and the mixture is allowed to stand at room temperature for 30 minutes and evaporated to dryness with a rotary evaporator. The residue is washed with hot anhydrous ethanol (about 40 ml), dissolved in methanol, and concentrated, and the precipitated colorless solid is collected by filtration to give the title compound 10 (650 mg) in 94% yield.

mp. 155° C. (decomposition)

Elemental Analysis:

Calcd (for C$_{19}$H$_{32}$N$_2$O$_{14}$Pt)(%): C, 32.25; H, 4.56; N, 3.96.

Found (%): C, 29.32; H, 4.86; N, 3.95. IR: $\nu_{max}^{Nujol}$ 3300 (—OH), 3219, 3114 (—NH$_2$), 1620 (—C=O) cm$^{-1}$.

We claim:

1. An organo-platinum complex of the formula:

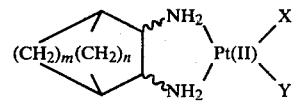

wherein X and Y each or taken together is a mono- or bi-functional ligand selected from the group consisting of halogeno, nitrato, sulfonato, monocarboxylato (mono-functional), sulfato, and dicarboxylato (bi-functional);

and each of n and m is an integer of 1 or 2.

2. An organo-platinum complex claimed in claim 1, wherein either n or m is an integer of 1 and the other is an integer of 2.

3. An organo-platinum complex claimed in claim 1, wherein X and Y each is halogeno.

4. An organo-platinum complex claimed in claim 1, wherein X and Y each is nitrato.

5. An organo-platinum complex claimed in claim 1, wherein X and Y each is chloroacetato.

6. An organo-platinum complex claimed in claim 1, wherein X and Y each is glycolato.

7. An organo-platinum complex claimed in claim 1, wherein X and Y each is glucuronato.

8. An organo-platinum complex claimed in claim 1, wherein X and Y taken together is sulfato.

9. An organo-platinum complex claimed in claim 1, wherein X and Y taken together is oxalato.

10. An organo-platinum complex claimed in claim 1, wherein X and Y taken together is malonato.

11. An organo-platinum complex claimed in claim 1, namely dichloro[exo,cis-2,3-diaminobicyclo(2.2.1)heptane]platinum(II).

12. An organo-platinum compex claimed in claim 1, namely dinitrato[exo,cis-2,3-diaminobicyclo(2.2.1)heptane]platinum(II).

13. An organo-platinum complex, claimed in claim 1, namely sulfato[exo,cis-2,3-diaminobicyclo(2.2.1)heptane]platinum(II).

14. An organo-platinum complex claimed in claim 1, namely malonato[exo,cis-2,3-diaminobicyclo(2.2.1)heptane]platinum(II).

15. An organo-platinum complex, claimed in claim 1, namely bis(chloroacetato)[exo,cis-2,3-diaminobicyclo(2.2.1)heptane]platinum(II).

16. An organo-platinum complex claimed in claim 1, namely hemimellitato[exo,cis-2,3-diaminobicyclo(2.2.1-)heptane]platinum(II).

17. An organo-platinum complex claimed in claim 1, namely oxalato[exo,cis-2,3-diaminobicyclo(2.2.1)heptane]platinum(II).

18. An organo-platinum complex claimed in claim 1, namely bis(glycolato)[exo,cis-2,3-diaminobicyclo(2.2.1-)heptane]platinum(II).

19. An organo-platinum complex, claimed in claim 1, namely bis(glucuronato)[exo,cis-2,3-diaminobicyclo(2.2.1)heptane]platinum(II).

* * * * *